(12) United States Patent
Arnelle et al.

(10) Patent No.: US 9,040,552 B2
(45) Date of Patent: May 26, 2015

(54) SELECTIVE OPIOID COMPOUNDS

(71) Applicant: Alkermes, Inc.

(72) Inventors: Derrick Arnelle, Arlington, MA (US); Daniel Deaver, Franklin, MA (US); Reginald L. Dean, III, Boxborough, MA (US); Mark Todtenkopf, Franklin, MA (US)

(73) Assignee: Alkermes, Inc., Waltham, MA (US)

( * ) Notice: Subject to any disclaimer, the term of this patent is extended or adjusted under 35 U.S.C. 154(b) by 97 days.

(21) Appl. No.: 13/693,662

(22) Filed: Dec. 4, 2012

(65) Prior Publication Data
US 2014/0005215 A1    Jan. 2, 2014

Related U.S. Application Data

(62) Division of application No. 12/371,334, filed on Feb. 13, 2009, now Pat. No. 8,354,534.

(60) Provisional application No. 61/028,780, filed on Feb. 14, 2008, provisional application No. 61/087,295, filed on Aug. 8, 2008.

(51) Int. Cl.
| | |
|---|---|
| A61K 31/485 | (2006.01) |
| A61K 45/06 | (2006.01) |
| C07D 221/28 | (2006.01) |
| C07D 489/00 | (2006.01) |
| C07D 489/08 | (2006.01) |
| C07D 471/08 | (2006.01) |

(52) U.S. Cl.
CPC ............ *C07D 489/08* (2013.01); *A61K 31/485* (2013.01); *A61K 45/06* (2013.01); *C07D 471/08* (2013.01)

(58) Field of Classification Search
CPC ............................ C07D 471/08; C07D 489/08
USPC ...................................................... 546/44, 74
See application file for complete search history.

(56) References Cited

U.S. PATENT DOCUMENTS

| 4,730,048 | A | 3/1988 | Portoghese |
| 5,739,145 | A | 4/1998 | Nagase et al. |
| 8,772,308 | B2 | 7/2014 | Zhang et al. |
| 2006/0063792 | A1* | 3/2006 | Dolle et al. ................ 514/282 |

FOREIGN PATENT DOCUMENTS

| JP | 61271275 A | 12/1986 |
| JP | 2011512360 A | 4/2011 |
| WO | 02080918 A | 10/2002 |
| WO | 2007/031284 A1 | 3/2007 |

OTHER PUBLICATIONS

Cancer and Metastasis Reviews (1998), 17(1), 91-106.*
Science (1999), vol. 286, 531-536.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org|wiki|Cancer.*
Irritable Bowel Syndrome [online]. Retrieved on Nov. 4, 2014 from the internet. URL http://digestive.niddk.nih.gov/ddiseases/pubs/ibs/.*

\* cited by examiner

*Primary Examiner* — Shawquia Jackson
(74) *Attorney, Agent, or Firm* — Elmore Patent Law Group, P.C.; Roy P. Issac; Carolyn S. Elmore

(57) ABSTRACT

The present invention relates to compounds of Formula I or II, or pharmaceutically acceptable salts, esters, or prodrugs thereof:

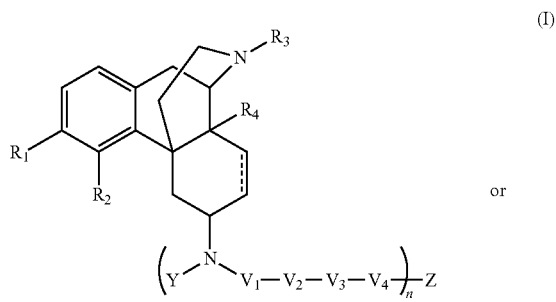

or

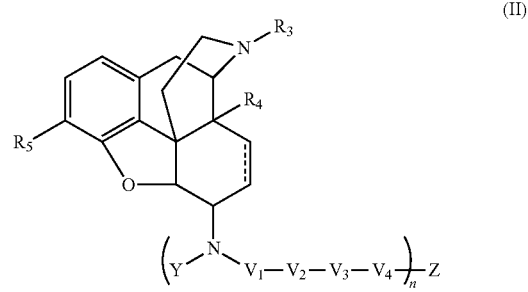

which relates to mophinan compounds useful as μ, δ and/or κ receptor opioid compounds and pharmaceuticals containing same that may be useful for mediating analgesia, combating drug addiction, alcohol addiction, drug overdose, mental illness, bladder dysfunctions, neurogenic bladder, interstitial cystitis, urinary incontinence, premature ejaculation, inflammatory pain, peripherally mediated and neuropathic pain, cough, lung edema, diarrhea, cardiac disorders, cardioprotection, depression, and cognitive, respiratory, diarrhea, irritable bowel syndrome and gastro-intestinal disorders, immunomodulation, and anti-tumor agents.

14 Claims, 1 Drawing Sheet

SELECTIVE OPIOID COMPOUNDS

RELATED APPLICATIONS

This application is a divisional of U.S. application Ser. No. 12/371,334, filed Feb. 13, 2009 and claims the benefit of U.S. provisional application No. 61/028,780 filed Feb. 14, 2008 and 61/087,295 filed Aug. 8, 2008. The contents of the above applications are incorporated herein by reference.

TECHNICAL FIELD

This invention relates to morphinan compounds useful as $\mu$, $\kappa$ and/or $\delta$ receptor opioid compounds and pharmaceuticals containing same that may be useful for mediating analgesia, combating drug addiction, alcohol addiction, drug overdose, mental illness, bladder dysfunctions, neurogenic bladder, interstitial cystitis, urinary incontinence, premature ejaculation, inflammatory pain, peripherally mediated and neuropathic pain, cough, lung edema, diarrhea, cardiac disorders, cardioprotection, depression, and cognitive, respiratory, diarrhea, irritable bowel syndrome and gastro-intestinal disorders, immunomodulation, and as anti-tumor agents.

BACKGROUND OF THE INVENTION

Opioid drugs typically target three types of endogenous opioid receptors (i.e., $\mu$, $\delta$, and $\kappa$ receptors) in biological systems. Many opiates, such as morphine, are $\mu$ opioid agonists that are often used as analgesics for the treatment of severe pain due to their activation of $\mu$ opioid receptors in the brain and central nervous system (CNS). Opioid receptors are, however, not limited to the CNS, and may be found in other tissues throughout the body, i.e., peripheral to the CNS. A number of side effects of opioid drugs may be caused by activation of these peripheral receptors. For example, administration of $\mu$ opioid agonists often results in intestinal dysfunction due to the large number of receptors in the wall of the gut (Wittert, G., Hope, P. and Pyle, D., *Biochemical and Biophysical Research Communications*, 1996, 218, 877-881; Bagnol, D., Mansour, A., Akil, A. and Watson, S. J., *Neuroscience*, 1997, 81, 579-591). Specifically, opioids are generally known to cause nausea and vomiting, as well as inhibition of normal propulsive gastrointestinal function in animals and man (Reisine, T., and Pasternak, G., Goodman & Gilman's *The Pharmacological Basis of Therapeutics*, Ninth Edition, 1996, 521-555), resulting in side effects such as, for example, constipation.

It would be of benefit to inhibit the natural activity of endogenous opioids during and/or after periods of biological stress, such as surgery and childbirth, so that ileus and related forms of bowel dysfunction can be prevented and/or treated. Currently, therapies for ileus include functional stimulation of the intestinal tract, stool softeners, laxatives, lubricants, intravenous hydration, and nasogastric decompression. These prior art methods suffer from drawbacks, for example, as lacking specificity for post-surgical or post-partum ileus. And these prior art methods offer no means for prevention. If ileus could be prevented, hospital stays, recovery times, and medical costs would be significantly decreased, in addition to the benefit of minimizing patient discomfort. Thus, drugs that selectively act on opioid receptors in the gut would be ideal candidates for preventing and/or treating post-surgical and post-partum ileus. Of those, drugs that do not interfere with the effects of opioid analgesics in the CNS would be of special benefit in that they could be administered simultaneously for pain management with limited side effects.

Peripheral opioid antagonists that do not cross the blood-brain barrier into the CNS are known in the literature and have been tested in relation to their activity on the GI tract. In U.S. Pat. No. 5,250,542, U.S. Pat. No. 5,434,171, U.S. Pat. No. 5,159,081, and U.S. Pat. No. 5,270,328, peripherally selective piperidine-N-alkylcarboxylate opioid antagonists are described as being useful in the treatment of idiopathic constipation, irritable bowel syndrome, and opioid-induced constipation. Some peripheral $\mu$ antagonists derived from the structure naltrexone have been reported in the literature (U.S. Pat. No. 4,806,556; Botros, et al., *J. Med. Chem.* 1989, 32, 2068-2071). In addition, U.S. Pat. No. 4,176,186 describes quaternary derivatives of noroxymorphone (i.e., methylnaltrexone) that are said to prevent or relieve the intestinal immobility side effect of narcotic analgesics without reducing analgesic effectiveness. U.S. Pat. No. 5,972,954 describes the use of methylnaltrexone, enteric-coated methylnaltrexone, or other quaternary derivatives of noroxymorphone for preventing and/or treating opioid- and/or nonopioid-induced side effects associated with opioid administration.

General opioid antagonists, such as naloxone and naltrexone, have also been implicated as being useful in the treatment of GI tract dysmotility. For example, U.S. Pat. No. 4,987,126 and Kreek, M. J. Schaefer, R. A., Hahn, E. F., Fishman, J. Lancet, 1983, 1, 8319, 261 disclose naloxone and other morphinan-based opioid antagonists (i.e., naloxone, naltrexone) for the treatment of idiopathic gastrointestinal dysmotility. In addition, naloxone has been shown to effectively treat non-opioid induced bowel obstruction, implying that the drug may act directly on the GI tract or in the brain (Schang, J. C., Devroede, G., Am. J. Gastroenerol., 1985, 80, 6, 407). Furthermore, it has been implicated that naloxone may provide therapy for paralytic ileus (Mack, D. J. Fulton, J. D., Br. J. Surg., 1989, 76, 10, 1101). However, it is well known that activity of naloxone and related drugs is not limited to peripheral systems and may interfere with the analgesic effects of opioid narcotics.

Despite recent advances in peripherally acting opioids, there is still a need for more effective and safe opioid compounds, with potent $\mu$, $\kappa$, and/or $\delta$ receptor agonist activities that produce essentially no central mechanism side effect, more particularly for the use in preventing or treating undesirable side effects associated with administering exogenous opioids with minimal impact on opioid agonist analgesia.

SUMMARY OF THE INVENTION

The present invention relates to derivatives of morphinans and 3-carboxamido-6-amino-substituted 4,5 epoxymorphinans to target modulation of opioid receptor activity outside of the CNS, particularly those receptors associated with the gastrointestinal tract, by reducing the lipid permeability of the drug either in the gastrointestinal tract or at the blood-brain barrier (BBB).

Accordingly, the present invention provides a compound having a general formula I or II:

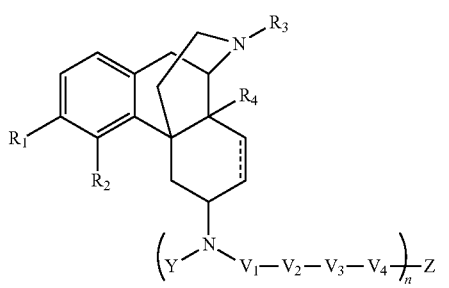

(I)

or

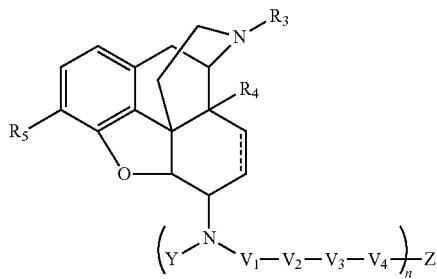

(II)

or its geometric isomers, enantiomers, diastereomers, racemates, pharmaceutically acceptable salts, prodrugs and solvates thereof, wherein:

$R_1$ is selected from the group consisting of: hydrogen, halogen, $OR_a$, $SR_a$, $S(O)R_a$, $SO_2R_a$, $S(O)NR_bR_c$, $SO_2NR_bR_c$, $NR_b$-Q-$R_c$, CN, (C=W)$NR_bR_c$, C(O)$OR_a$, $CH_2OR_a$, $CH_2NR_bR_c$, heteroaryl, and substituted heteroaryl;

$R_a$, $R_b$, $R_c$ are each independently selected from:
(i) hydrogen;
(ii) aryl; substituted aryl; heteroaryl; substituted heteroaryl;
(iii) heterocyclic or substituted heterocyclic; and
(iv) —$C_1$-$C_8$ alkyl, —$C_2$-$C_8$ alkenyl, or —$C_2$-$C_8$ alkynyl each containing 0, 1, 2, or 3 or more heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

alternatively, $R_b$ and $R_c$ are taken together with the attached nitrogen atom to form a heterocyclic or substituted heterocyclic;

Q is absent or selected from (C=O), (SO$_2$), (C=NH), (C=S), or (CONR$_a$);

W is O, S, NOR$_a$ or NR$_a$;

$R_2$ is independently selected from the group consisting of hydrogen, halogen, $OR_a$, $SR_a$, $NR_bR_c$; alternatively, $R_1$ and $R_2$ are taken together with the carbon they attached to form a heteroaryl, substituted heteroaryl, heterocyclic or substituted heterocylic;

$R_3$ is independently selected from the group consisting of:
(i) hydrogen;
(ii) aryl; substituted aryl; heteroaryl; substituted heteroaryl;
(iii) heterocyclic or substituted heterocyclic; and
(iv) —$C_1$-$C_8$ alkyl, —$C_2$-$C_8$ alkenyl, or —$C_2$-$C_8$ alkynyl each containing 0, 1, 2, or 3 or more heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 or more heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

$R_4$ is hydrogen, $OR_a$, or $NR_b$-$Q^1$-$R_c$, where $Q^1$ is absent or selected from (C=O) or (SO$_2$);

$R_5$ is selected from the group consisting of: hydrogen, halogen, $SR_a$, $S(O)R_a$, $SO_2R_a$, $S(O)NR_bR_c$, $SO_2NR_bR_c$, $NR_b$-Q-$R_c$, CN, (C=W)$NR_bR_c$, C(O)$OR_a$, $CH_2OR_a$, $CH_2NR_bR_c$, heteroaryl, and substituted heteroaryl;

Y is hydrogen, lower alkyl, or lower alkoxy;

$V_1$ is C=O, SO$_2$, $C_1$-$C_6$ alkylene, substituted alkylene, $C_2$-$C_6$ alkenylene, $C_2$-$C_6$ alkynylene; $V_2$ is absent, alkylene, substituted alkylene, $C_2$-$C_6$ alkenylene, $C_2$-$C_6$ alkynylene; heterocyclic, heteroaryl, aryl or C=O; $V_3$ is absent, alkylene, substituted alkylene, $C_2$-$C_6$ alkenylene, $C_2$-$C_6$ alkynylene; heterocyclic, heteroaryl, aryl or C=O; $V_4$ is absent, alkylene, substituted alkylene, $C_2$-$C_6$ alkenylene, $C_2$-$C_6$ alkynylene; heterocyclic, heteroaryl, aryl or C=O;

n is 1, 2, 3 or 4; wherein each repeating unit can be the same or different;

Z is hydrogen, $NR_bR_c$, (C=W)$NR_bR_c$, $NR_a$(C=W)$NR_bR_c$, (C=W)OH, C(O)NHOH, heteroaryl, or substituted heteroaryl;

alternatively,

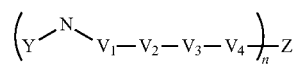

can be selected from the group consisting of natural or unnatural amino acids and peptidomimetics; and ==== denotes a carbon-carbon single or double bond.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
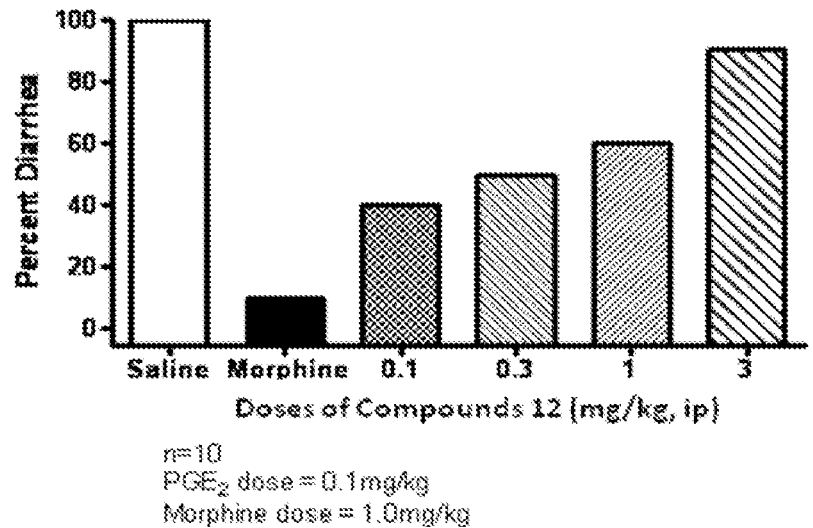
FIG. 1: Inhibition of morphine blockade of PGE$_2$-induced diarrhea by compound-12.

A first embodiment of the invention is a compound represented by Formula I or II as described above, or a pharmaceutically acceptable salts, esters or prodrugs thereof, alone or in combination with a pharmaceutically acceptable carrier or excipient.

In one embodiment of the invention are compounds represented by Formula III or IV:

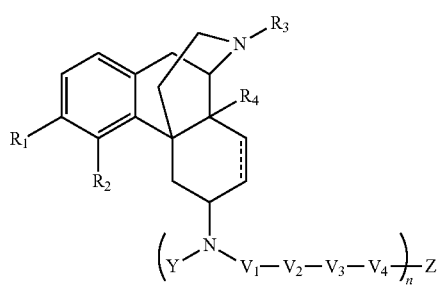

(III)

or

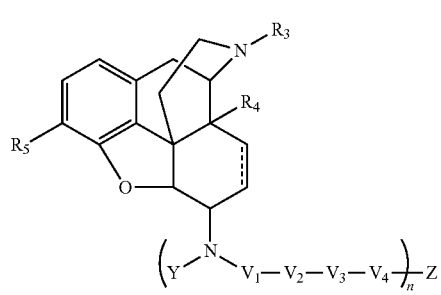

(IV)

or a pharmaceutically acceptable salt, ester or prodrug thereof, alone or in combination with a pharmaceutically acceptable carrier or excipient, where n, $R_1$, $R_2$, $R_3$, $R_4$, $R_5$, Y, $V_1$, $V_2$, $V_3$, $V_4$ and Z are as defined above.

In one embodiment of the invention are compounds represented by Formula V:

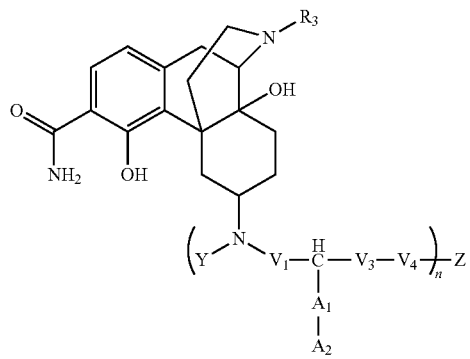

(V)

or a pharmaceutically acceptable salt, ester or prodrug thereof, alone or in combination with a pharmaceutically acceptable carrier or excipient, where $A_1$ is absent, $C_1$-$C_6$ alkylene, substituted alkylene, $C_2$-$C_6$ alkenylene, $C_2$-$C_6$ alkynylene; $A_2$ hydrogen, $NR_bR_c$, (C=W)$NR_bR_c$, $NR_a$(C=W)$NR_bR_c$, (C=W)OH, heteroaryl or substituted heteroaryl; and n, $R_3$, $V_1$, $V_3$, $V_4$, W, $R_a$, $R_b$, $R_c$ and Z are as defined above. In one example,

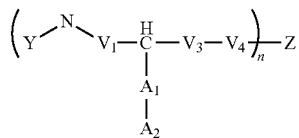

is selected from the group consisting of lysine (K), arginine (R), histidine (H), aspartic acid (D), glutamic acid (E) or combinations thereof.

In one embodiment of the invention are compounds represented by Formula VI:

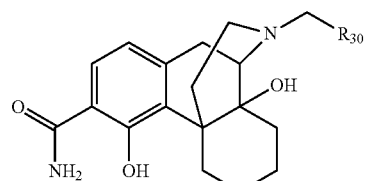

(VI)

or a pharmaceutically acceptable salt, ester or prodrug thereof, alone or in combination with a pharmaceutically acceptable carrier or excipient, wherein $R_{30}$ is hydrogen, lower alkyl, lower alkenyl, lower alkynyl, $C_3$-$C_6$ cycloalkyl, $C_3$-$C_6$ cycloalkenyl, heterocyclic or substituted heterocyclic; where $A_1$ is absent, $C_1$-$C_6$ alkylene, substituted alkylene, $C_2$-$C_6$ alkenylene, $C_2$-$C_6$ alkynylene; $A_2$ hydrogen, $NR_bR_c$, (C=W)$NR_bR_c$, $NR_a$(C=W)$NR_bR_c$, (C=W)OH, heteroaryl or substituted heteroaryl; and n, $R_3$, $V_1$, $V_3$, $V_4$, W, $R_a$, $R_b$, $R_c$ and Z are as defined above. In one example,

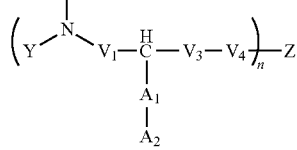

is selected from the group consisting of lysine (K), arginine (R), histidine (H), aspartic acid (D), glutamic acid (E) or combinations thereof.

In one embodiment of the invention are compounds represented by Formula VII:

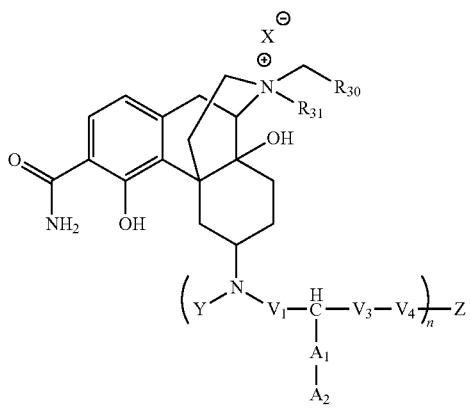

(VII)

or a pharmaceutically acceptable salt, ester or prodrug thereof, alone or in combination with a pharmaceutically acceptable carrier or excipient, wherein $X^-$ is counterion selected from the group consisting of halide, sulfate, phosphate, nitrate, and anionic-charged organic species; $R_{30}$, and $R_{31}$ are independently hydrogen, lower alkyl, lower alkenyl, lower alkynyl, $C_3$-$C_6$ cycloalkyl, $C_3$-$C_6$ cycloalkenyl, heterocyclic or substituted heterocyclic; where $A_1$ is absent, $C_1$-$C_6$ alkylene, substituted alkylene, $C_2$-$C_6$ alkenylene, $C_2$-$C_6$ alkynylene; $A_2$ hydrogen, $NR_bR_c$, (C=W)$NR_bR_c$, $NR_a$(C=W)$NR_bR_c$, (C=W)OH, heteroaryl or substituted heteroaryl; and n, $R_3$, $V_1$, $V_3$, $V_4$, W, $R_a$, $R_b$, $R_c$ and Z are as defined above. In one example,

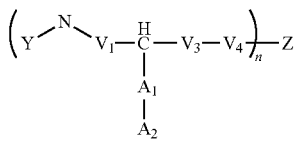

is selected from the group consisting of lysine (K), arginine (R), histidine (H), aspartic acid (D), glutamic acid (E) or combinations thereof.

In one embodiment of the invention are compounds represented by Formula VIII:

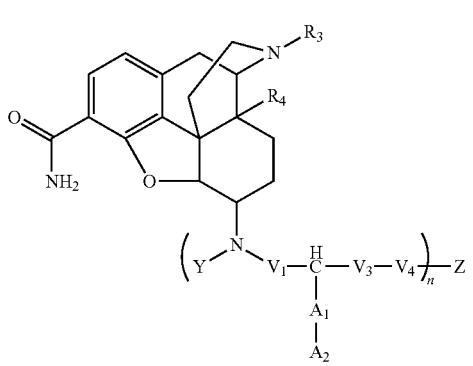

(VIII)

or a pharmaceutically acceptable salt, ester or prodrug thereof, alone or in combination with a pharmaceutically acceptable carrier or excipient, where $A_1$ is absent, $C_1$-$C_6$ alkylene, substituted alkylene, $C_2$-$C_6$ alkenylene, $C_2$-$C_6$ alkynylene; $A_2$ hydrogen, $NR_bR_c$, (C=W)$NR_bR_c$, $NR_a$(C=W)$NR_bR_c$, (C=W)OH, heteroaryl or substituted heteroaryl; and n, $R_3$, $V_1$, $V_3$, $V_4$, W, $R_a$, $R_b$, $R_c$ and Z are as defined above. In one example,

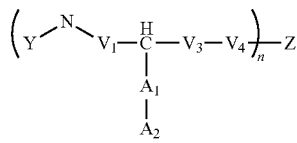

is selected from the group consisting of lysine (K), arginine (R), histidine (H), aspartic acid (D), glutamic acid (E) or combinations thereof.

In one embodiment of the invention are compounds represented by Formula IX:

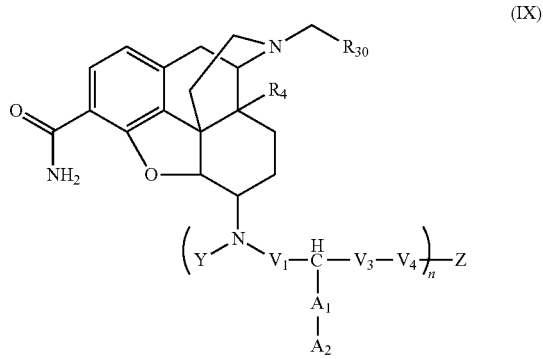

(IX)

or a pharmaceutically acceptable salt, ester or prodrug thereof, alone or in combination with a pharmaceutically acceptable carrier or excipient, wherein $R_{30}$ is hydrogen, lower alkyl, lower alkenyl, lower alkynyl, $C_3$-$C_6$ cycloalkyl, $C_3$-$C_6$ cycloalkenyl, heterocyclic or substituted heterocyclic; $A_1$ is absent, $C_1$-$C_6$ alkylene, substituted alkylene, $C_2$-$C_6$ alkenylene, $C_2$-$C_6$ alkynylene; $A_2$ hydrogen, $NR_bR_c$, (C=W)$NR_bR_c$, $NR_a$(C=W)$NR_bR_c$, (C=W)OH, heteroaryl or substituted heteroaryl; n, Y, $V_1$, $V_3$, $V_4$, W, $R_a$, $R_b$, $R_c$ and Z are as defined above. In one example,

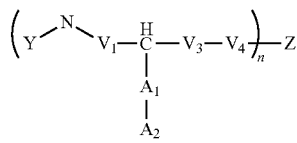

is selected from the group consisting of lysine (K), arginine (R), histidine (H), aspartic acid (D), glutamic acid (E) or combinations thereof.

In one embodiment of the invention are compounds represented by Formula X:

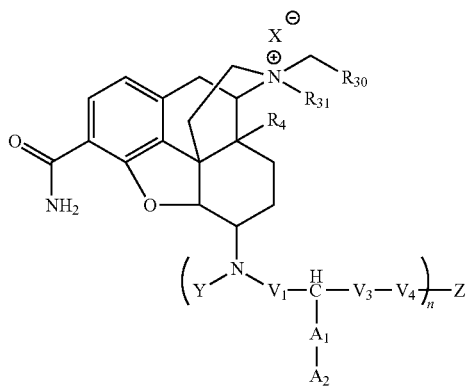

(X)

or a pharmaceutically acceptable salt, ester or prodrug thereof, alone or in combination with a pharmaceutically acceptable carrier or excipient, wherein $X^-$ is counterion selected from the group consisting of halide, sulfate, phosphate, nitrate, and anionic-charged organic species; $R_{30}$ and $R_{31}$ are independently hydrogen, lower alkyl, lower alkenyl, lower alkynyl, $C_3$-$C_6$ cycloalkyl, $C_3$-$C_6$ cycloalkenyl, heterocyclic or substituted heterocyclic; where $A_1$ is absent, $C_1$-$C_6$ alkylene, substituted alkylene, $C_2$-$C_6$ alkenylene, $C_2$-$C_6$ alkynylene; $A_2$ hydrogen, $NR_bR_c$, (C=W)$NR_bR_c$, $NR_a$(C=W)$NR_bR_c$, (C=W)OH, heteroaryl or substituted heteroaryl; and n, $R_3$, $V_1$, $V_3$, $V_4$, W, $R_a$, $R_b$, $R_c$ and Z are as defined above. In one example,

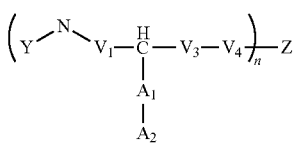

is selected from the group consisting of lysine (K), arginine (R), histidine (H), aspartic acid (D), glutamic acid (E) or combinations thereof.

Representative compounds according to the invention are those selected from the TABLE A below or its geometric isomers, enantiomers, diastereomers, racemates, pharmaceutically acceptable salts, prodrugs and solvates thereof:

TABLE A

| Compound No. | Structure |
|---|---|
| 1 | (structure shown) |
| 2 | (structure shown) |
| 3 | (structure shown) |
| 4 | (structure shown) |
| 5 | (structure shown) |

TABLE A-continued

| Compound No. | Structure |
|---|---|
| 6 | *(structure image)* |
| 7 | *(structure image)* |
| 8 | *(structure image)* |
| 9 | *(structure image)* |
| 10 | *(structure image)* |
| 11 | *(structure image)* |
| 12 | *(structure image)* |

TABLE A-continued

| Compound No. | Structure |
|---|---|
| 13 | 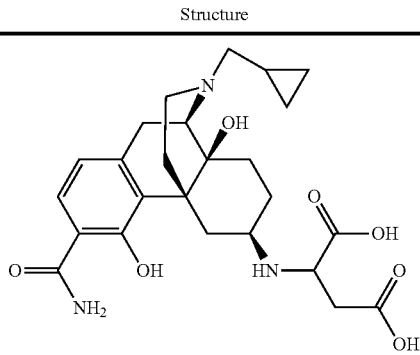 |

In one embodiment, the compound of the invention is administered to antagonize the peripheral side effects of an opioid, wherein the compound of the present invention does not substantially cross the blood-brain barrier nor does it decrease the beneficial activity of the opioid. The phrase "does not substantially cross," as used herein, means that less than about 20% by weight of the compound employed in the present methods crosses the blood-brain barrier, preferably less than about 15% by weight, more preferably less than about 10% by weight, even more preferably less than about 5% by weight and most preferably 0% by weight of the compound crosses the blood-brain barrier. Selected compounds can be evaluated for CNS penetration by determining plasma and brain levels following I.V. administration.

In one embodiment of the present invention, the compositions of the invention may further comprise at least one opioid. A wide variety of opioids is available that may be suitable for use in the present methods and compositions. In preferred embodiments, the present methods and compositions may involve an opioid that is selected from alfentanil, buprenorphine, diprenorphine, etorphine, nalorphine, naltrindole, butorphanol, codeine, dezocine, dihydrocodeine, fentanyl, hydrocodone, hydromorphone, levorphanol, meperidine (pethidine), methadone, naltrexone, naloxone, nalmefene, nalmexone, morphine, nalbuphine, oxycodone, oxymorphone, pentazocine, propiram, propoxyphene, sufentanil and/or tramadol. More preferably, the opioid is selected from morphine, naltrexone, naloxone, codeine, oxycodone, hydrocodone, dihydrocodeine, propoxyphene, fentanyl, tramadol, and mixtures thereof.

The compounds of the invention may further comprise one or more other active ingredients that may be conventionally employed in analgesic and/or cough-cold-antitussive combination products. Such conventional ingredients include, for example, aspirin, acetaminophen, phenylpropanolamine, phenylephrine, chlorpheniramine, caffeine, and/or guaifenesin. Typical or conventional ingredients that may be included in the opioid component are described, for example, in the *Physicians' Desk Reference,* 1999, the disclosure of which is hereby incorporated herein by reference, in its entirety.

In one embodiment, the compositions of the invention may further comprise one or more compounds that may be designed to enhance the analgesic potency of the opioid and/or to reduce analgesic tolerance development. Such compounds include, for example, dextromethorphan or other NMDA antagonists (Mao, M. J. et al., Pain, 1996, 67, 361), L-364,718 and other CCK antagonists (Dourish, C. T. et al., Eur. J. Pharmacol., 1988, 147, 469), NOS inhibitors (Bhargava, H. N. et al., *Neuropeptides,* 1996, 30, 219), PKC inhibitors (Bilsky, E. J. et al., *J. Pharmacol. Exp. Ther.,* 1996, 277, 484), and dynorphin antagonists or antisera (Nichols, M. L. et al., *Pain,* 1997, 69, 317). The disclosures of each of the foregoing documents are hereby incorporated herein by reference, in their entireties.

In one embodiment, the compounds of the invention can be used in methods for preventing or treating post-operative or opioid-induced ileus. In another embodiment, the compounds of the invention can be used as as analgesics, anesthetics, anti-pruritics, anti-diarrheal agents, anti-convulsants, anti-tussives, and/or anorexics.

The compounds of the present invention may be used in methods to bind μ opioid receptors. Such binding may be accomplished by contacting the receptor with an effective amount of the compound of the invention. The opioid receptors may be located in the central nervous system or located peripherally to the central nervous system or in both locations. Preferably, the contacting step conducted in an aqueous medium, preferably at physiologically relevant ionic strength, pH, and the like.

In one embodiment, the compounds are opioid receptor agonists. In another embodiment, the compounds prevent or treat a condition or disease caused by an opioid (either endogenous or exogenous). In yet another embodiment, particularly where the opioid are exogenous, the compounds of the invention preferably do not substantially cross the blood-brain barrier.

In one embodiment, the compounds antagonize the activity of the opioid receptors. In other preferred embodiments, the compounds prevent or treat a condition or disease caused by a δ, κ, or μ opioid (either endogenous or exogenous). In other embodiment, particularly where the opioids are exogenous, the compounds of the invention preferably do not substantially cross the blood-brain barrier.

The compounds of the present invention may be used in methods to antagonize opioid receptors, particularly where undesirable symptoms or conditions are side effects of administering exogenous opioids. Furthermore, the compounds of the invention may be used to treat patients having disease states that are ameliorated by binding opioid receptors or in any treatment wherein temporary suppression of the μ opioid receptor system is desired.

Such symptoms, conditions or diseases include the complete or partial antagonism of opioid-induced sedation, confusion, respiratory depression, euphoria, dysphoria, hallucinations, pruritus (itching), increased biliary tone, increased biliary colic, and urinary retention, ileus, emesis, and addiction liability; prevention or treatment of opioid and cocaine dependence; rapid opioid detoxification; treatment of alcoholism; treatment of alcoholic coma; detection of opioid use or abuse (pupil test); treatment of eating disorders; treatment of obesity; treatment of post-concussional syndrome; adjunctive therapy in septic, hypovolemic or endotoxin-induced shock; potentiation of opioid analgesia (especially at ultralow doses); reversal or prevention of opioid tolerance and physical dependence (especially at ultra-low doses); prevention of sudden infant death syndrome; treatment of psychosis (especially wherein the symptoms are associated with schizophrenia, schizophreniform disorder, schizoaffective disorder, unipolar disorder, bipolar disorder, psychotic depression, Alzheimer's disease, Parkinson's disease, compulsive disorders, and other psychiatric or neurologic disorders with psychosis as symptoms); treatment of dyskinesia, treatment of autism; treatment of the endocrine system (including increased release of leutinizing hormone, treatment of infertility, increasing number of multiple births in animal husbandry, and male and female sexual behavior); treatment of the immune system and cancers associated with binding of the opioid receptors; treatment of anxiolysis; treatment of diuresis; treatment and regulation of blood pressure; treatment of tinnitus or impaired hearing; treatment of epilepsy; treatment of cachexia; treatment of general cognitive dysfunctions; and treatment of kleptomania.

The compounds of the present invention may also be used as cytostatic agents, as antimigraine agents, as immunomodulators, as immunosuppressives, as antiarthritic agents, as antiallergic agents, as virucides, to treat diarrhea, antipsychotics, as antischizophrenics, as antidepressants, as uropathic agents, as antitussives, as antiaddictive agents, as anti-smoking agents, to treat alcoholism, as hypotensive agents, to treat and/or prevent paralysis resulting from traumatic ischemia, general neuroprotection against ischemic trauma, as adjuncts to nerve growth factor treatment of hyperalgesia and nerve grafts, as anti-diuretics, as stimulants, as anti-convulsants, or to treat obesity. Additionally, the present compounds may be used in the treatment of Parkinson's disease as an adjunct to L-dopa for treatment dyskinesia associated with the L-dopa treatment.

In certain embodiments, the compounds of the invention may be used in methods for preventing or treating gastrointestinal dysfunction, including, but not limited to, irritable bowel syndrome, opioid-bowel dysfunction, colitis, post-operative and opioid-induced emesis (nausea and vomiting), decreased gastric motility and emptying, inhibition of small and/or large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, and delayed absorption of orally administered medications or nutritive substances.

DEFINITIONS

Listed below are definitions of various terms used to describe this invention. These definitions apply to the terms as they are used throughout this specification and claims, unless otherwise limited in specific instances, either individually or as part of a larger group.

The term "peripheral" or "peripherally" designates that the compound acts primarily on physiological systems and components external to the central nervous system. In preferred form, the peripheral opioid antagonist compounds employed in the methods of the present invention exhibit high levels of activity with respect to peripheral tissue, such as, gastrointestinal tissue, while exhibiting reduced, and preferably substantially no CNS activity.

The phrase "side effect" refers to a consequence other than the one(s) for which an agent or measure is used, as the adverse effects produced by a drug, especially on a tissue or organ system other then the one sought to be benefited by its administration. In the case, for example, of opioids, the term "side effect" may refer to such conditions as, for example, respiratory depression, acute sedation, constipation, opioid-induced bowel dysfunction, nausea and/or vomiting.

The term "unnatural amino acid" refers to any derivative of a natural amino acid including D forms, and α- and β-amino acid derivatives. It is noted that certain amino acids, e.g., hydroxyproline, that are classified as a non-natural amino acid herein, may be found in nature within a certain organism or a particular protein. Amino acids with many different protecting groups appropriate for immediate use in the solid phase synthesis of peptides are commercially available. In addition to the twenty most common naturally occurring amino acids, the following examples of non-natural amino acids and amino acid derivatives may be used according to the invention (common abbreviations in parentheses): β-alanine (β-ALA), γ-aminobutyric acid (GABA), 2-aminobutyric acid (2-Abu), α,β-dehydro-2-aminobutyric acid (8-AU), 1-aminocyclopropane-1-carboxylic acid (ACPC), aminoisobutyric acid (Aib), 2-amino-thiazoline-4-carboxylic acid, 5-aminovaleric acid (5-Ava), 6-aminohexanoic acid (6-Ahx), 8-aminooctanoic acid (8-Aoc), 11-aminoundecanoic acid (11-Aun), 12-aminododecanoic acid (12-Ado), 2-aminobenzoic acid (2-Abz), 3-aminobenzoic acid (3-Abz), 4-aminobenzoic acid (4-Abz), 4-amino-3-hydroxy-6-methylheptanoic acid (Statine, Sta), aminooxyacetic acid (Aoa), 2-aminotetraline-2-carboxylic acid (ATC), 4-amino-5-cyclohexyl-3-hydroxypentanoic acid (ACHPA), para-aminophenylalanine (4-$NH_2$-Phe), biphenylalanine (Bip), para-bromophenylalanine (4-Br-Phe), ortho-chlorophenylalanine] (2-Cl-Phe), meta-chlorophenylalanine (3-Cl-Phe), para-chlorophenylalanine (4-Cl-Phe), meta-chlorotyrosine (3-Cl-Tyr), para-benzoylphenylalanine (Bpa), tert-butylglycine (TLG), cyclohexylalanine (Cha), cyclohexylglycine (Chg), 2,3-diaminopropionic acid (Dpr), 2,4-diaminobutyric acid (Dbu), 3,4-dichlorophenylalanine (3,4-$Cl_2$-Phe), 3,4-difluorophenylalanine (3,4-$F_2$-Phe), 3,5-diiodotyrosine (3,5-$I_2$-Tyr), ortho-fluorophenylalanine (2-F-Phe), meta-fluorophenylalanine (3-F-Phe), para-fluorophenylalanine (4-F-Phe), meta-fluorotyrosine (3-F-Tyr), homoserine (Hse), homophenylalanine (Hfe), homotyrosine (Htyr), 5-hydroxytryptophan (5-OH-Trp), hydroxyproline (Hyp), para-iodophenylalanine (4-1-Phe), 3-iodotyrosine (3-1-Tyr), indoline-2-carboxylic acid (Idc), isonipecotic acid (Inp), meta-methyltyrosine (3-Me-Tyr), 1-naphthylalanine (1-Nal), 2-naphthylalanine (2-Nal), para-nitrophenylalanine (4-$NO_2$-Phe), 3-nitrotyrosine (3-$NO_2$-Tyr), norleucine (Nle), norvaline (Nva), ornithine (Orn), ortho-phosphotyrosine ($H_2PO_3$-Tyr), octahydroindole-2-carboxylic acid (Oic), penicillamine (Pen), pentafluorophenylalanine ($F_5$-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), and thiazolidine-4-carboxylic acid (thioproline, Th). Additionally, N-alkylatd amino acids may be used, as well as amino acids having amine-containing side chains (such as Lys and Orn) in which the amine has been acylated or or alkylated.

The term "peptide mimetic" or "peptidomimetic" means a molecule able to mimic the biological activity of an amino acid or peptide but is no longer peptidic in chemical nature. By strict definition, a peptidomimetic is a molecule that no longer contains any peptide bonds (that is, amide bonds between amino acids). However, the term peptide mimetic is sometimes used to describe molecules that are no longer completely peptidic in nature, such as pseudo-peptides, semi-peptides and peptoids. Whether completely or partially non-peptide, peptidomimetics according to this invention provide a spatial arrangement of reactive chemical moieties that closely resembles the three-dimensional arrangement of active groups in the amino acid or peptide on which the peptidomimetic is based. As a result of this similar active-site geometry, the peptidomimetic has effects on biological systems, which are similar to the biological activity of the amino acid or peptide.

The term "$C_1$-$C_6$ alkyl," or "$C_1$-$C_8$ alkyl," as used herein, refer to saturated, straight- or branched-chain hydrocarbon radicals containing from one to six, or from one to eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The term "$C_2$-$C_6$ alkenyl," or "$C_2$-$C_8$ alkenyl," as used herein, denote a group derived from a hydrocarbon moiety, wherein the hydrocarbon moiety has at least one carbon-carbon double bond and contains from two to six, or two to eight, carbon atoms, respectively. Alkenyl groups include, but are not limited to, for example, ethenyl, propenyl, butenyl, 1-methyl-2-buten-1-yl, heptenyl, octenyl and the like.

The term "$C_2$-$C_6$ alkynyl," or "$C_2$-$C_8$ alkynyl," as used herein, denote a group derived from a hydrocarbon moiety, wherein the hydrocarbon moiety has at least one carbon-carbon triple bond and contains from two to six, or two to eight, carbon atoms, respectively. Representative alkynyl groups include, but are not limited to, for example, ethynyl, 1-propynyl, 1-butynyl, heptynyl, octynyl and the like.

The term "$C_3$-$C_8$-cycloalkyl", or "$C_3$-$C_{12}$-cycloalkyl," as used herein, denotes a group derived from a monocyclic or polycyclic saturated carbocyclic ring compound by the removal of a single hydrogen atom where the saturated carbocyclic ring compound has from 3 of 8, or from 3 to 12, ring atoms, respectively. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl.

The term "$C_3$-$C_8$-cycloalkenyl", or "$C_3$-$C_{12}$-cycloalkenyl" as used herein, denote a group derived from a monocyclic or polycyclic carbocyclic ring compound having at least one carbon-carbon double bond, where the carbocyclic ring compound has from 3 to 8, or from 3 to 12, ring atoms, respectively. Examples of $C_3$-$C_8$-cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, and the like.

The term "aryl," as used herein, refers to a mono-, bi-, or tricyclic carbocyclic ring system having one or two aromatic rings including, but not limited to, phenyl, naphthyl, tetrahydronaphthyl, indanyl, idenyl and the like.

The term "arylalkyl," as used herein, refers to a $C_1$-$C_3$ alkyl or $C_1$-$C_6$ alkyl residue attached to an aryl ring. Examples include, but are not limited to, benzyl, phenethyl and the like.

The term "heteroaryl," as used herein, refers to a mono-, bi-, or tri-cyclic aromatic radical or ring having from five to 15 ring atoms of which at least one ring atom is selected from S, O and N; wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroarylalkyl," as used herein, refers to a $C_1$-$C_3$ alkyl or $C_1$-$C_6$ alkyl residue residue attached to a heteroaryl ring. Examples include, but are not limited to, pyridinylmethyl, pyrimidinylethyl and the like.

The term "substituted" as used herein, refers to independent replacement of one, two, or three or more of the hydrogen atoms thereon with substituents including, but not limited to, —F, —Cl, —Br, —I, —OH, protected hydroxy, —NO$_2$, —CN, —NH$_2$, N$_3$, protected amino, alkoxy, thioalkoxy, oxo, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkynyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_{12}$-alkenyl, —NHCO$_2$—$C_2$-$C_{12}$-alkynyl, —NHCO$_2$—$C_3$-$C_{12}$-cycloalkyl, —NHCO$_2$— aryl, —NHCO$_2$— heteroaryl, —NHCO$_2$-heterocycloalkyl, —NHC(O)NH$_2$, —NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, —NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl-SO$_2$NH$_2$, —SO$_2$NH—$C_1$-$C_{12}$-alkyl, —SO$_2$NH—$C_2$-$C_{12}$-alkenyl, —SO$_2$NH—$C_2$-$C_{12}$-alkynyl, —SO$_2$NH—$C_3$-$C_{12}$-cycloalkyl, —SO$_2$NH— aryl, —SO$_2$NH— heteroaryl, —SO$_2$NH— heterocycloalkyl, —NHSO$_2$—$C_1$-$C_{12}$-alkyl, —NHSO$_2$—$C_2$-$C_{12}$-alkenyl, —NHSO$_2$—$C_2$-$C_{12}$-alkynyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, methylthiomethyl, or -L'-R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. It is understood that the aryls, heteroaryls, alkyls, and the like can be further substituted. In some cases, each substituent in a substituted moiety is additionally optionally substituted with one or more groups, each group can include —F, —Cl, —Br, —I, —OH, —NO$_2$, —CN, or —NH$_2$ or the like.

In accordance with the invention, any of the aryls, substituted aryls, heteroaryls and substituted heteroaryls described herein, can be any type of aromatic group.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a group derived from a monocyclic or polycyclic saturated carbocyclic ring compound. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

The term "heterocycloalkyl" and "heterocyclic" can be used interchangeably and refer to a non-aromatic 3-, 4-, 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (v) any of the above rings may be fused to a benzene ring, and (vi) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted to give substituted heterocyclic.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, hetoerarylalkylene and heterocycloalkylene groups are to be included in the above definitions, and are applicable to provide the formulas herein with proper valency.

The term "hydroxy activating group", as used herein, refers to a labile chemical moiety which is known in the art to activate a hydroxy group so that it will depart during synthetic procedures such as in a substitution or elimination reactions. Examples of hydroxy activating group include, but not limited to, mesylate, tosylate, triflate, p-nitrobenzoate, phosphonate and the like.

The term "activated hydroxy", as used herein, refers to a hydroxy group activated with a hydroxy activating group, as defined above, including mesylate, tosylate, triflate, p-nitrobenzoate, phosphonate groups, for example.

The term "protected hydroxy," as used herein, refers to a hydroxy group protected with a hydroxy protecting group, as defined below, including benzoyl, acetyl, trimethylsilyl, triethylsilyl, methoxymethyl groups.

The terms "halo" and "halogen," as used herein, refer to an atom selected from fluorine, chlorine, bromine and iodine.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described herein, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G., S. M. Wuts, *Protective Groups in Organic Synthesis,* 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$).

Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

PHARMACEUTICAL COMPOSITIONS

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide or polylactide-co-glycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

In one embodiment, administration of the microparticles comprising iloprost or another pharmaceutical agent to be administered in addition to iloprost provides local or plasma concentrations sustained at approximately constant values over the intended period of release (e.g., up to 2 to 24 hours, to enable dosing once, twice, three times, four times or more than four times per day). The microparticle formulations may allow patients to take treatments less frequently, and to receive more prolonged and steadier relief.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Suitable daily oral dosages for the compounds of the inventions described herein are on the order of about 0.01 mg to about 1,000 mg of each active agent described herein. Desirably, each oral dosage contains from 0.01 to 1,000 mg/day, particularly 0.01, 0.05, 0.1, 0.2, 0.5, 1.0, 2.5, 5, 10, 15, 20, 25, 30, 40, 50, 75, 100, 125, 150, 175, 200, 225, 250, 500, 750, 850 and 1,000 milligrams/day of each active ingredient in the composition of the present invention (e.g. each opioid antagonist and each peripherally restricted opioid agonist) administered for the treatment of a reward dysfunction disorder. The specific dose level for any particular patient will vary depending upon a variety of factors, including but not limited to, the activity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

Dosing schedules may be adjusted to provide the optimal therapeutic response. For example, administration can be one to three times daily for a time course of one day to several days, weeks, months, and even years, and may even be for the life of the patient. Practically speaking, a unit dose of any given composition of the invention or active agent can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth.

The weight ratio of the active agents in the instant combination therapy (e.g. an opioid antagonist and a peripherally restricted opioid agonist) may be varied and will depend upon the effective dose of each ingredient. Generally, an effective dose of each will be used. Thus, for example, when an opioid antagonist is combined with a peripherally restricted opioid agonist the weight ratio of the opioid antagonist to the peripherally restricted opioid will generally range from about 1000:1 to about 1:1000, preferably about 5, 10, 15, 20, 25, 30, 40, 50, 75, 100, 125, 150, 175, 200, 225, 250, 500, 750, 850 and 1,000:1 to about 1:5, 10, 15, 20, 25, 30, 40, 50, 75, 100, 125, 150, 175, 200, 225, 250, 500, 750, 850 and 1,000. Compositions of the agents in the combinations of the present invention (e.g. an opioid antagonist and a peripherally restricted opioid agonist) will generally also be within the aforementioned range, but in each case, an effective dose of each active ingredient should be used.

Pharmaceutical kits useful in, for example, the treatment of pain, which comprise a therapeutically effective amount of an opioid along with a therapeutically effective amount of the morphinan compound of the invention, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL® two-part container (available from Abbott Labs, Chicago, Ill.), as desired. The opioid compound and the compounds of the invention may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Unless otherwise defined, all technical and scientific terms used herein are accorded the meaning commonly known to one with ordinary skill in the art. All publications, patents, published patent applications, and other references mentioned herein are hereby incorporated by reference in their entirety.

ABBREVIATIONS

Abbreviations which have been used in the descriptions of the schemes and the examples that follow are:
ACN for acetonitrile;
Ac for acetyl;
Boc for tert-butoxycarbonyl;
Bz for benzoyl;
Bn for benzyl;
CDI for carbonyldiimidazole;
dba for dibenzylidene acetone;
CDI for 1,1'-carbonyldiimidizole;
DBU for 1,8-diazabicyclo[5.4.0]undec-7-ene;
DCM for dichloromethane;
DIAD for diisopropylazodicarboxylate;
DMAP for dimethylaminopyridine;
DMF for dimethyl formamide;
DMSO for dimethyl sulfoxide;
dppb for diphenylphosphino butane;
EtOAc for ethyl acetate;
HATU for 2-(7-Aza-1H-benzotriazole-1-yl)-1,1,3,3-tetramethyluronium hexafluorophosphate;
iPrOH for isopropanol;
NaHMDS for sodium bis(trimethylsilyl)amide;
NMO for N-methylmorpholine N-oxide;
MeOH for methanol;
Ph for phenyl;
POPd for dihydrogen dichlorobis(di-tert-butylphosphino) palladium(II);
TBAHS for tetrabutyl ammonium hydrogen sulfate;
TEA for triethylamine;
THF for tetrahydrofuran;
TPP for triphenylphosphine;
Tris for Tris(hydroxymethyl)aminomethane;
BME for 2-mercaptoethanol;
BOP for benzotriazol-1-yloxy-tris(dimethylamino)phosphonium hexafluorophosphate;
COD for cyclooctadiene;
DAST for diethylaminosulfur trifluoride;
DABCYL for 6-(N-4'-carboxy-4-(dimethylamino)azobenzene)-aminohexyl-1-O-(2-cyanoethyl)-(N,N-diisopropyl)-phosphoramidite;
DCM for dichloromethane;
DIAD for diisopropyl azodicarboxylate;
DIBAL-H for diisobutylaluminum hydride;
DIEA for diisopropyl ethylamine;
DMAP for N,N-dimethylaminopyridine;
DME for ethylene glycol dimethyl ether;
DMEM for Dulbecco's Modified Eagles Media;
DMF for N,N-dimethyl formamide;
DMSO for dimethylsulfoxide;
EDANS for 5-(2-Amino-ethylamino)-naphthalene-1-sulfonic acid;
EDCI or EDC for 1-(3-diethylaminopropyl)-3-ethylcarbodiimide hydrochloride;
EtOAc for ethyl acetate;
HATU for O (7-Azabenzotriazole-1-yl)-N,N,N',N'-tetramethyluronium hexafluorophosphate;
Hoveyda's Cat. for Dichloro(o-isopropoxyphenylmethylene) (tricyclohexylphosphine)ruthenium(II);
KHMDS is potassium bis(trimethylsilyl) amide;
Ms for mesyl;
EtOAc for ethyl acetate;
g for gram(s);
h for hour(s);
NMM for N-4-methylmorpholine;
PyBrOP for Bromo-tri-pyrrolidino-phosphonium hexafluorophosphate;
Ph for phenyl;
RCM for ring-closing metathesis;
RT for reverse transcription;
RT-PCR for reverse transcription-polymerase chain reaction;
TEA for triethyl amine;
TFA for trifluoroacetic acid;
MeOH for methanol;
mg for milligram(s);
min for minute(s);
MS for mass spectrometry;
NMR for nuclear magnetic resonance;
rt for room temperature;
THF for tetrahydrofuran;
TLC for thin layer chromatography;
TPP or PPh$_3$ for triphenylphosphine;
tBOC or Boc for tert-butyloxy carbonyl; and
Xantphos for 4,5-Bis-diphenylphosphanyl-9,9-dimethyl-9H-xanthene.

SYNTHETIC METHODS

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

The morphinan compounds according to the present invention may be synthesized employing methods taught, for example, in U.S. Pat. No. 5,250,542, U.S. Pat. No. 5,434,171, U.S. Pat. No. 5,159,081, and U.S. Pat. No. 5,270,328, the disclosures of which are hereby incorporated herein by reference in their entireties. The optically active and commercially available naltrexone was employed as starting material in the synthesis of the present compounds may be prepared by the general procedure taught in U.S. Pat. No. 3,332,950, the disclosure of which is hereby incorporated herein by reference in its entirety.

Scheme 1 exemplified one method of preparing the compounds of the invention.

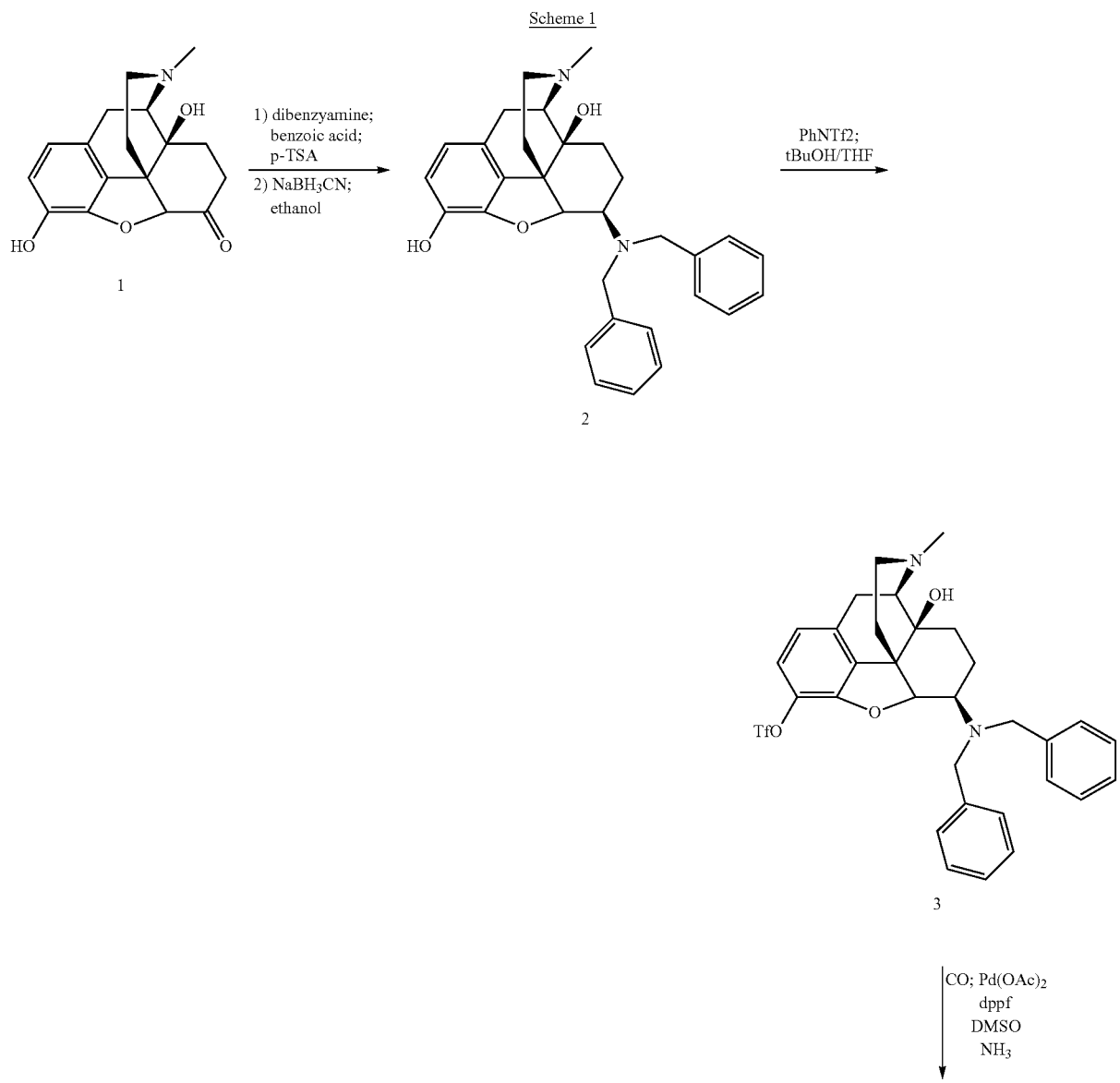

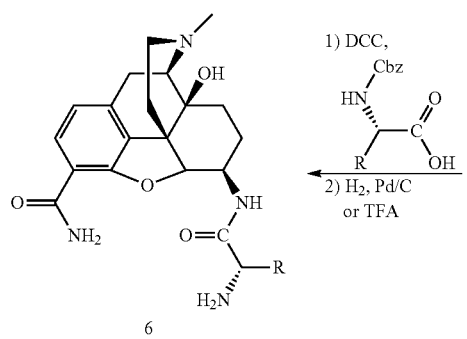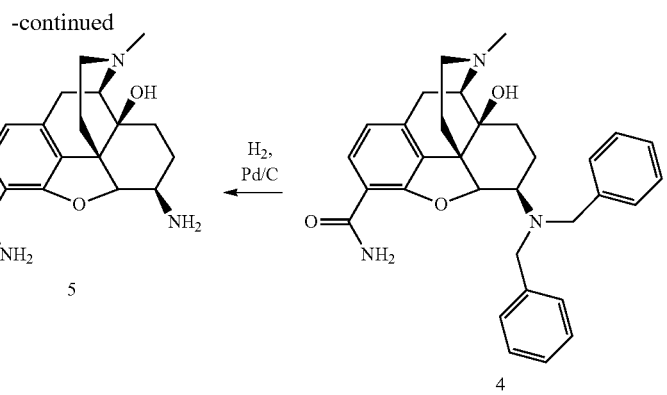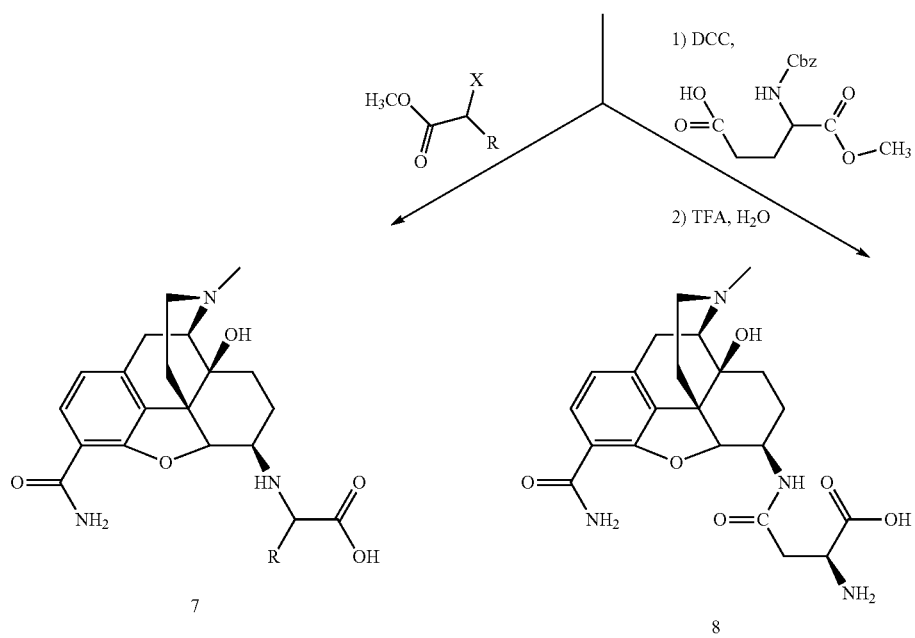

Biological Assays

The potencies of the compounds are determined by testing the ability of a range of concentrations of each compound to inhibit the binding of the non-selective opioid antagonist, [$^3$H]diprenorphine, to the cloned human μ, κ, and δ opioid receptors, expressed in separate cell lines. $IC_{50}$ values are obtained by nonlinear analysis of the data using GraphPad Prism version 5.00 for Windows (GraphPad Software, San Diego). $K_i$ values are obtained by Cheng-Prusoff corrections of $IC_{50}$ values.

Receptor Binding (In Vitro Assay)

The receptor binding method (DeHaven and DeHaven-Hudkins, "Characterization of Opioid Receptors", Current Protocols in Pharmacology (Eds. Enna S J and Williams M) 1.4.1-1.4.12, John Wiley & Sons, Inc., New York (1998)) is a modification of the method of Raynor, et al., Mol. Pharmacol. 45:330-334 (1994). Stable cell lines expressing the individual full-length human mu, delta, and kappa opioid receptor cDNAs were generated by transfecting 70% confluent Chinese hamster ovary (CHO)-K1 cells in 35-mm dishes with the appropriate cDNA construct. Cells harvested 72 h after transfection were centrifuged at 1000 g for 10 min; resuspended in 50 mM TriszHCl, pH 7.8, containing 1 mM EGTA, 5 mM $MgCl_2$, 10 mg/liter leupeptin, 10 mg/liter pepstatin A, 200 mg/liter bacitracin, and 0.5 mg/liter aprotinin; and centrifuged as before. The pellet was resuspended in the same buffer, and the cells were homogenized using a Polytron homogenizer. The homogenate was centrifuged at 48,000 g for 20 min at 4° C., the membrane pellet was resuspended at 1 mg protein/ml in the same buffer as before, and the aliquots were stored at 80° C. until use. Experiments were conducted by incubating a final concentration of 25 to 100 mg of protein and 1 nM [3H]diprenorphine per tube with or without cold drug in the buffer described above in a final assay volume of 500 ml for 1 h at room temperature. After incubation at room temperature for one hour, the samples were filtered through GF/B filters that had been pre-soaked in a solution of 0.5% (w/v) polyethylenimine and 0.1% (w/v) bovine serum albumin in water. The filters were rinsed 4 times with 1 mL of cold 50 mM Tris HCl, pH 7.8 and radioactivity remaining on the filters determined by scintillation spectroscopy. Nonspecific binding was determined by the minimum values of the titration curves and was confirmed by separate assay wells containing 10 μM naloxone. $K_i$ values were determined by Cheng-Prusoff corrections of $IC_{50}$ values derived from non-linear regression fits of 12 point titration curves using GraphPad Prism® version 5.00 for Windows (GraphPad Software, San Diego, Calif.).

To determine the equilibrium dissociation constant for the inhibitors ($K_i$), radioligand bound (cpm) in the presence of various concentrations of test compounds was measured. The concentration to give half-maximal inhibition (IC$_{50}$) of radioligand binding was determined from a best nonlinear regression fit to the following equation, $$Y = \text{Bottom} + \frac{(\text{Top} - \text{Bottom})}{1 + 10^{x - LogIC50}}$$

where Y was the amount of radioligand bound at each concentration of test compound, Bottom was the calculated amount of radioligand bound in the presence of an infinite concentration of test compound, Top was the calculated amount of radioligand bound in the absence of test compound, X was the logarithm of the concentration of test compound, and Log IC$_{50}$ was the log of the concentration of test compound where the amount of radioligand bound was halfway between Top and Bottom. The nonlinear regression fit was performed using the program Prism® (GraphPad Software, San Diego, Calif.). The K$_i$ values are then determined from the EC$_{50}$ values by the following equation, $$Ki = \frac{EC_{50}}{1 + \frac{[\text{Ligand}]}{K_d}}$$

where [ligand] was the concentration of radioligand and K$_d$ was the equilibrium dissociation constant for the radioligand.

Opioid Receptor Mediated [$^{35}$S] GTPγS Binding

The potencies of the antagonists were assessed by their abilities to inhibit agonist-stimulated [$^{35}$S]GTPγS binding to membranes containing the cloned human μ, κ, or δ opioid receptors. The agonists used are loperamide for the μ opioid receptor, U50488H for the κ opioid receptor, and BW373U86 for the δ opioid receptor.

To determine the IC$_{50}$ value, which was the concentration to give half-maximal inhibition of agonist-stimulated [$^{35}$S] GTPγS binding, the amount of [$^{35}$S]GTPγS bound in the presence of a fixed concentration of agonist and various concentrations of antagonist was measured. The fixed concentration of agonist is the EC$_{80}$ for the agonist, which was the concentration to give 80% of the relative maximum stimulation of [$^{35}$S]GTPγS binding. The IC$_{50}$ value was determined from a best nonlinear regression fit of the data to the following equation, $$Y = \text{Bottom} + \frac{(\text{Top} - \text{Bottom})}{1 + 10^{x - LogIC50}}$$

where Y was the amount of [$^{35}$S]GTPγS bound at each concentration of antagonist, Bottom was the calculated amount of [$^{35}$S]GTPγS bound in the presence of an infinite concentration of antagonist, Top was the calculated amount of [$^{35}$S] GTPγS bound in the absence of added antagonist, X is the logarithm of the concentration of antagonist, and Log IC$_{50}$ was the logarithm of the concentration of antagonist where the amount of [$^{35}$S]GTPγS bound was halfway between Bottom and Top. The nonlinear regression fit was performed using GraphPad Prism® version 5.00 for Windows (GraphPad Software, San Diego, Calif.).

Antagonism of Morphine-Inhibited Diarrhea in Mice (In Vivo Assay)

Albino mice of either sex (Swiss-Webster) weighing 20-30 g were used to determine the ability of an opioid antagonist to antagonize morphine inhibition of prostaglandin E2 (PGE$_2$) induced diarrhea according to the method of Dajani et al. (1979). Briefly, mice are treated at time 0 with morphine, 1 mg/kg s.c. and an opioid antagonist, 60, 180, 240, 300, 360, 480, or 720 mg/kg orally; or 3, 10, 30, 100 or 140 mg/kg i.p; or saline, 0.1 ml/10 gm body weight orally or i.p. Mice are then treated at 30 min with PGE$_2$, 320 μg/kg which consistently produced watery stools in the absence of morphine. The pie-shaped cages were observed at 15 mins for the presence of absence of watery stools. Eleven to 24 mice were used per dose of an opioid antagonist for the oral and 6 are used for the i.p. routes. Data was analyzed using Fisher's exact probability test (Siegel, 1956). These studies were repeated using naltrexone, 0.005, 0.01, 0.05, 0.1, and 5 mg/kg i.p. and 0.5, 1, 2, and 4 mg/kg orally.

Antagonism of Morphine-Induced Antinociception in Mice (In Vivo Assay)

Albino mice of either sex (Swiss-Webster) weighing 20-30 g were used to determine the ability of an opioid antagonist to antagonize morphine-induced antinociception. Antinociception was measured using the hotplate method of Eddy et al. (1950; 1953). The hot plate surface temperature was maintained at 55° C. and the test session was not allowed to go beyond 60 seconds.

Figure 2:
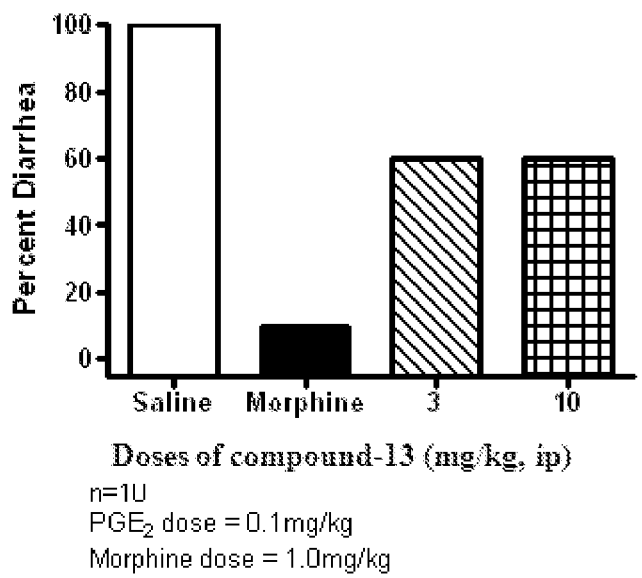
FIG. 2: Inhibition of morphine blockade of PGE$_2$-induced diarrhea by compound-13.

Mice were tested for a non-drug baseline response at time 0. After the test, mice are treated with morphine, 15 mg/kg i.p. and 15 minutes later are treated with an opioid antagonist, 10 and 30 mg/kg i.p. or saline, 0.1 ml/10 g body weight i.p followed by test at 45 min. Ten mice were used per dose of an opioid antagonist. The mean pretreatment response times were compared to the maximum response times obtained after morphine administration. An increase in response of 45 or more seconds was judged as antinociception. A statistically significant reduction in the morphine-related response time was taken as a reversal of the morphine effect. The number of mice demonstrating antinociception on the hot plate test after treatment with saline or an opioid antagonist 10 and 30 mg/kg were compared using a one-way ANOVA. FIGS. 1 and 2 show the inhibition of morphine blockade of PGE$_2$-induced diarrhea by compound-12.

Mouse Gastrointestinal Transit (GIT) Assay (In Vivo Assay)

Male Swiss-Webster mice (25-30 g) obtained from Charles River Laboratories are used for all experiments. Mice are housed 5/cage in polycarbonate cages with food and water available ad libitum. Mice are on a 12 hours light:dark schedule with lights on at 6:30 a.m. All experiments are performed during the light cycle. Mice are fasted the night before the experiment, with water available ad libitum.

Mice are administered vehicle (water) or test compound (10 mg/kg) orally 2 or 6 hour before determination of GIT. Compounds are administered in a volume of 0.1 ml/10 g of body weight. Morphine (1-3 mg/kg) or vehicle (0.9% saline) is administered s.c. 35 minutes prior to determination of GIT. Ten minutes after the morphine treatment, mice are administered 0.2 ml of a charcoal meal orally. The charcoal meal consisted of a slurry of charcoal, flour, and water in the following ratio (1:2:8, w:w:v). Twenty-five minutes after receiving the charcoal meal, the mice are euthanized with CO$_2$ and the intestines are removed. GIT is determined with GIT expressed as the % GIT by the following formula:

$$\frac{\text{(distance to leading edge of charcoal meal (cm))}}{\text{(total length of the small intestine (cm))}} \times 100$$

For each compound a % Antagonism (% A) value is determined for the 2 and 6 hour antagonist pretreatment. Using the mean % GIT for each treatment group, % A is calculated using the following formula:

$$1 = \frac{\left(\left(\text{mean vehicle response} - \frac{}{\text{mean antagonist} + \text{morphine response}}\right)\right)}{(\text{mean vehicle response} - \text{mean morphine response})} \times 100$$

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

What is claimed:

1. A method of treating a condition or disease associated with binding opioid receptors in a patient in need thereof, wherein the condition or disease is pain, gastrointestinal dysfunction, or ileus, comprising the step of: administering to said patient a composition comprising an effective amount of a compound of Formula I or II:

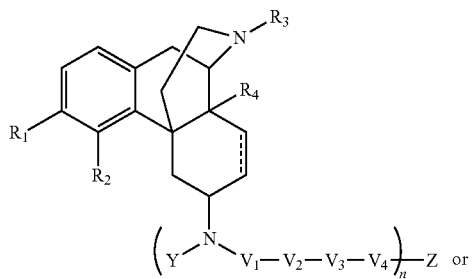
(I)

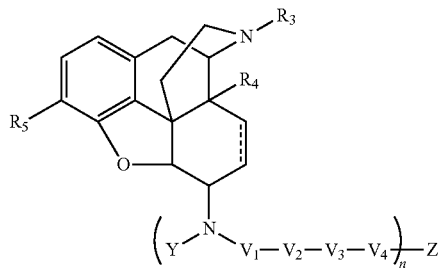
(II)

or its geometric isomers, enantiomers, diastereomers, racemates, pharmaceutically acceptable salts, prodrugs and solvates thereof, wherein:

$R_1$ is selected from the group consisting of: hydrogen, halogen, $OR_a$, $SR_a$, $S(O)R_a$, $SO_2R_a$, $S(O)NR_bR_c$, $SO_2NR_bR_c$, $NR_b$-Q-$R_c$, CN, (C=W)$NR_bR_c$, C(O)$OR_a$, $CH_2OR_a$, $CH_2NR_bR_c$, heteroaryl, and substituted heteroaryl;

$R_a$, $R_b$, $R_c$ are each independently selected from:
  (i) hydrogen;
  (ii) aryl; substituted aryl; heteroaryl; substituted heteroaryl;
  (iii) heterocyclic or substituted heterocyclic; and
  (iv) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

alternatively, $R_b$ and $R_c$ are taken together to form a heterocyclic or substituted heterocyclic;

Q is absent or selected from (C=O), ($SO_2$), (C=NH), (C=S), or (CONR$_a$);

W is O, S, NOR$_a$ or NR$_a$;

$R_2$ is independently selected from the group consisting of hydrogen, halogen, $OR_a$, $SR_a$, $NR_bR_c$;

alternatively, $R_1$ and $R_2$ are taken together to form a heteroaryl, substituted heteroaryl, heterocyclic or substituted heterocylic;

$R_3$ is independently selected from the group consisting of:
  (v) hydrogen;
  (vi) aryl; substituted aryl; heteroaryl; substituted heteroaryl;
  (vii) heterocyclic or substituted heterocyclic; and
  (viii) —$C_1$-$C_8$ alkyl, —$C_2$-$C_8$ alkenyl, or —$C_2$-$C_8$ alkynyl each containing 0, 1, 2, or 3 or more heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 or more heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

$R_4$ is hydrogen, $OR_a$, or $NR_b$-$Q^1$-$R_c$, where $Q^1$ is absent or selected from (C=O) or ($SO_2$);

$R_5$ is selected from the group consisting of: hydrogen, halogen, $SR_a$, $S(O)R_a$, $SO_2R_a$, $S(O)NR_bR_c$, $SO_2NR_bR_c$, $NR_b$-Q-$R_c$, CN, (C=W)$NR_bR_c$, C(O)$OR_a$, $CH_2OR_a$, $CH_2NR_bR_c$, heteroaryl, and substituted heteroaryl;

Y is hydrogen, lower akyl, or lower alkoxy;

$V_1$ is C=O, $C_1$-$C_6$ alkylene or substituted alkylene; $V_2$ is absent, alkylene, substituted alkylene, or C=O; $V_3$ is absent; $V_4$ is absent;

n is 1, 2, 3 or 4; wherein each repeating unit can be the same or different;

Z is hydrogen, (C=W)OH or C(O)NHOH; alternatively,

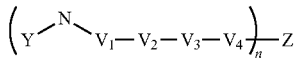

can be selected from the group consisting of natural or unnatural amino acids; and ═══ denotes a carbon-carbon single or double bond.

2. The method according to claim 1, wherein the binding antagonizes the activity of the opioid receptors.

3. The method of claim 1, wherein the ileus is post-operative ileus.

4. A method according to claim 1, wherein the condition is pain and the composition further comprises an effective amount of an opioid.

5. The method according to claim 2, wherein the compound binds to the opioid receptors.

6. The method according to claim 5, wherein the μ opioid receptors are located in the central nervous system.

7. The method according to claim 5, wherein the μ opioid receptors are located peripherally to the central nervous system.

8. The method according to claim 2, wherein the compound does not substantially cross the blood-brain barrier.

9. The method of treating a side effect associated with an opioid, wherein the side effect is selected from the group consisting of constipation, opioid-induced bowel dysfunction, nausea, vomiting, and combinations thereof, comprising the step of: administering to a patient in need thereof, a composition comprising an effective amount of a compound of Formula I or II:

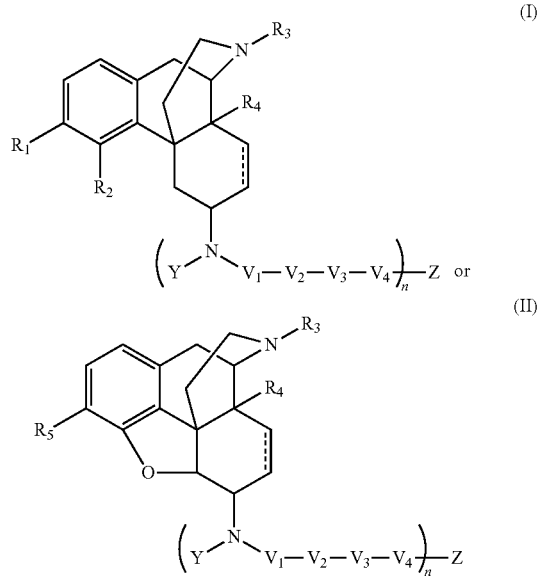

or its geometric isomers, enantiomers, diastereomers, racemates, pharmaceutically acceptable salts, prodrugs and solvates thereof, wherein:

$R_1$ is selected from the group consisting of: hydrogen, halogen, $OR_a$, $SR_a$, $S(O)R_a$, $SO_2R_a$, $S(O)NR_bR_c$, $SO_2NR_bR_c$, $NR_b$-Q-$R_c$, CN, (C=W)$NR_bR_c$, C(O)$OR_a$, $CH_2OR_a$, $CH_2NR_bR_c$, heteroaryl, and substituted heteroaryl;

$R_a$, $R_b$, $R_c$ are each independently selected from:
  (ix) hydrogen;
  (x) aryl; substituted aryl; heteroaryl; substituted heteroaryl;
  (xi) heterocyclic or substituted heterocyclic; and
  (xii) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

alternatively, $R_b$ and $R_c$ are taken together to form a heterocyclic or substituted heterocyclic;

Q is absent or selected from (C=O), ($SO_2$), (C=NH), (C=S), or (CON$R_a$);

W is O, S, $NOR_a$ or $NR_a$;

$R_2$ is independently selected from the group consisting of hydrogen, halogen, $OR_a$, $SR_a$, $NR_bR_c$;

alternatively, $R_1$ and $R_2$ are taken together to form a heteroaryl, substituted heteroaryl, heterocyclic or substituted heterocylic;

$R_3$ is independently selected from the group consisting of:
  (ix) hydrogen;
  (x) aryl; substituted aryl; heteroaryl; substituted heteroaryl;
  (xi) heterocyclic or substituted heterocyclic; and
  (xii) —$C_1$-$C_8$ alkyl, —$C_2$-$C_8$ alkenyl, or —$C_2$-$C_8$ alkynyl each containing 0, 1, 2, or 3 or more heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 or more heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

$R_4$ is hydrogen, $OR_a$, or $NR_b$-$Q^1$-$R_c$, where $Q^1$ is absent or selected from (C=O) or ($SO_2$);

$R_5$ is selected from the group consisting of: hydrogen, halogen, $SR_a$, $S(O)R_a$, $SO_2R_a$, $S(O)NR_bR_c$, $SO_2NR_bR_c$, $NR_b$-Q-$R_c$, CN, (C=W)$NR_bR_c$, C(O)$OR_a$, $CH_2OR_a$, $CH_2NR_bR_c$, heteroaryl, and substituted heteroaryl;

Y is hydrogen, lower akyl, or lower alkoxy;

$V_1$ is C=O, $C_1$-$C_6$ alkylene or substituted alkylene; $V_2$ is absent, alkylene, substituted alkylene, or C=O; $V_3$ is absent; $V_4$ is absent;

n is 1, 2, 3 or 4; wherein each repeating unit can be the same or different;

Z is hydrogen, (C=W)OH or C(O)NHOH; alternatively,

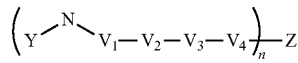

can be selected from the group consisting of natural or unnatural amino acids; and ═══ denotes a carbon-carbon single or double bond.

10. The method according to claim 9, wherein the opioid is endogenous.

11. The method according to claim 9, wherein the opioid is exogenous.

12. The method according to claim 9, wherein the composition further comprises an effective amount of at least one opioid.

13. The method according to claim 9, wherein the administering step occurs before, during or after a step of administering at least one opioid.

14. The method according to claim 12, wherein the opioid is alfentanil, buprenorphine, butorphanol, codeine, dezocine, dihydrocodeine, fentanyl, hydrocodone, hydromorphone, levorphanol, meperidine (pethidine), methadone, naloxone, naltrexone, morphine, nalbuphine, oxycodone, oxymorphone, pentazocine, propiram, propoxyphene, sufentanil, tramadol, or mixtures thereof.

* * * * *

UNITED STATES PATENT AND TRADEMARK OFFICE
CERTIFICATE OF CORRECTION

| | | |
|---|---|---|
| PATENT NO. | : 9,040,552 B2 | Page 1 of 1 |
| APPLICATION NO. | : 13/693662 | |
| DATED | : May 26, 2015 | |
| INVENTOR(S) | : Derrick Arnelle et al. | |

It is certified that error appears in the above-identified patent and that said Letters Patent is hereby corrected as shown below:

Claims

At Column 38

In claim 9, at line 20, delete "R" and insert -- Rc --.

Signed and Sealed this
Twenty-ninth Day of March, 2016

Michelle K. Lee
*Director of the United States Patent and Trademark Office*